(12) United States Patent
Brukner et al.

(10) Patent No.: US 6,333,177 B1
(45) Date of Patent: Dec. 25, 2001

(54) SELECTIVE TECHNIQUE FOR RAPID IDENTIFICATION OF PROTEINS AND GENES AND USES THEREOF

(75) Inventors: Ivan Brukner, Montréal; Noureddine Rouissi, Brossard; Abdellah Belmaaza, Laval, all of (CA)

(73) Assignee: Polygene Inc., Montreal (CA)

( * ) Notice: Subject to any disclaimer, the term of this patent is extended or adjusted under 35 U.S.C. 154(b) by 0 days.

(21) Appl. No.: 09/555,778

(22) PCT Filed: Dec. 1, 1998

(86) PCT No.: PCT/CA98/01111

§ 371 Date: Jul. 24, 2000

§ 102(e) Date: Jul. 24, 2000

(87) PCT Pub. No.: WO99/28497

PCT Pub. Date: Jun. 10, 1999

(30) Foreign Application Priority Data

Dec. 2, 1997 (CA) ..................... 2220785

(51) Int. Cl.[7] ............... C12P 19/34; C12Q 1/68
(52) U.S. Cl. ..................... 435/91.1; 435/6
(58) Field of Search ................ 435/6, 91.1

(56) References Cited

U.S. PATENT DOCUMENTS

| 5,270,163 | 12/1993 | Gold et al. | 435/6 |
| 5,567,588 | 10/1996 | Gold et al. | 435/6 |
| 5,712,375 | 1/1998 | Jensen et al. | 530/412 |

*Primary Examiner*—Kenneth R. Horlick
*Assistant Examiner*—Teresa Strzelecka
(74) *Attorney, Agent, or Firm*—Sughrue, Mion, PLLC (57) ABSTRACT

The current invention relates to a method for selecting oligonucleotides able of identifying differences at the molecular level between a plurality of biological systems. This method has been named "STRIPGEN" for "Selective Technique for Rapid Identification of Proteins and GENes". The STRIPGEN method involves selection of oligonucleotides having a higher affinity and specificity for target molecules of a first biological system and a lower affinity for binding target molecules of a second biological system. STRIPGEN is based on a sheme of positive selection over a first biological system and negative selection over a second biological system, and uses step-wise iterations of binding, separation and amplification. This method is very powerful since it can discriminate very subtle differences between biological systems of the same type such as between normal and abnormal cell types.

20 Claims, 6 Drawing Sheets

SCHEMATIC REPRESENTATION OF DIFFERENTIAL SELECTION

SCHEMATIC REPRESENTATION OF DIFFERENTIAL SELECTION

SELECTIVE TECHNIQUE FOR RAPID IDENTIFICATION OF PROTEINS AND GENES AND USES THEREOF

FIELD OF THE INVENTION

The current invention relates to a method for selecting oligonucleotides able of identifying differences at the molecular level between a plurality of biological systems. This method has been named "STRIPGEN" for "Selective Technique for Rapid identification of Proteins and GENes". The STRIPGEN method involves selection of oligonucleotides having a higher affinity and specificity for target molecules of a first biological system and a lower affinity for binding target molecules of a second biological system (and vice versa). STRIPGEN is based on a scheme of positive selection over a first biological system and negative selection over a second biological system. And uses step-wise iterations of binding, separation and amplification. This method is very powerful since it can discriminate very subtle differences between biological systems of the same type such as between normal and abnormal cell types.

DESCRIPTION OF THE PRIOR ART

Many if not all disorders have a genetic background. A genetic disorder finds its origin in the defect of one or a number of genes. The defect is generally a change in the roles of nucleotides in the DNA sequence coding for a protein. Any modification in the normal sequence of a gene (which usually codes for a specific sequence of amino acids in a protein) can after the original sequence of amino acids in a protein. A single defect in a gene can also produce changes in the primary structure of a protein, leading for example to changes in a protein's activity, improper or even absence of protein function, and over or under production of the protein within the cells. As proteins are essential to normal cellular structure and activities, an imbalance in the complex cellular system, even by a single protein, can result in a disease. Genetic defects can be found in either of the 100 000 to 150 000 genes that are distributed across the 23 pairs of human chromosomes. The discovery of causal genes and their protein products is of strategic importance in pharmaceutical terms as they provide powerful means for identifying the most important and significant targets for the development of novel diagnostic and therapeutic products.

Known in the art is a method called SELEX (Systematic Evolution of Ligands by EXponential enrichment). This method, which has been patented in the United States by NeXtar Pharmaceuticals Inc. (Boulder, Colo.) (U.S. Pat. No. 5,712,375), is used for identifying and preparing nucleic acid ligands to tissues. Similarly to the current application, the method described in U.S. Pat. No. 5,712,375 involves selection from a mixture of candidate oligonucleotides and step-wise iterations of binding, partitioning and amplification. Although not exemplified, U.S. Pat. No. 5,712,375 also claims for a method wherein a negative selection is performed in order to perfect the discrimination between subtle differences of similar tissue types.

However, unlike the method described in the current application, U.S. Pat. No. 5,712,375 does not suggest a method wherein a step of negative selection is performed Immediately after a step of positive selection. In contradiction to the current method, U.S. Pat. No. 5,712,375 suggests the performance of two or three rounds of negative selections only once a late-round, highly evolved pool of positively selected nucleic acid ligands have been obtained.

Although the method of U.S. Pat. No. 5,712,375 seems powerful, it is limited to biological tissue (single cells or aggregate of cells). Furthermore, since this method lacks an amplification step which the Applicant considers as essential, the method of U.S. Pat. No. 5,712,375 is much less specific and sensitive than the method of the current invention. As a result, the method of U.S. Pat. No. 5,712,375 has been successful only in demonstrating the identification of proteins in a biological tissue (i.e. non-soluble material). Neither this method nor any other method known to the Applicant has successfully shown the identification of soluble and non-soluble proteins which are present in a first biological system but are absent from a second similar biological system.

Therefore, there is a need for a rapid, efficient and simple method for producing oligonucleotides which are highly specific to target molecules, such as proteins, which are present in a first biological system but are absent from a second similar biological system.

SUMMARY OF THE INVENTION

The present invention includes methods for selecting oligonucleotides able of identifying at least one difference at the molecular level between at least two biological systems. These methods are very powerful since they can discriminate very subtle differences between biological systems of the same type such as between cells in different cell cycles, normal and pathological cells infected and non-infected cells, induced and non-Induced cells.

An Important object of the invention is to provide a method comprising the steps of:

a) contacting a pool of oligonucleotides with target molecules of a first biological system, wherein some of the oligonucleotides from the pool have an affinity for at least one of the target molecules of the first biological system;

b) separating the oligonucleotides having an affinity for the at least one target molecule from the remainder of the pool;

c) amplifying the oligonucleotides which have been separated in step b), to yield a pool enriched in oligonucleotides having a higher affinity for the at least one target molecule;

d) contacting the amplified oligonucleotides of step c) with target molecules of a second biological system;

e) removing the oligonucleotides having an affinity for any of the target molecules of said second biological system;

f) amplifying the remaining oligonucleotides to yield a pool of oligonucleotides having a higher affinity for at least one target molecule of the first biological system and a lower affinity for any of the target molecules of the second biological system; and g) repeating the combination of steps a) to f) until at least one difference is identified.

In a preferred embodiment, the above mentioned method is modified such that, in replacement of step g), the following steps are performed:

g) fractionating the amplified pool of step f) in at least two portions;

h) contacting a first pool's portion with target molecules of the first biological system and separating the at least one target molecule to which oligonucleotides have an affinity from the remainder of the target molecules; and i) repeating the combination of steps a) to h) until at least one difference is identified, wherein in at least one of the subsequent steps a):

a second pool's portion is used as the pool of oligonucleotides;

only the at least one target molecule separated in step h) is(are) used as target molecule(s) of the first biological system.

Preferably, step h) further comprises the substeps h') of contacting a third pool's portion with target molecules of the second biological system, and separating any target molecule of the second biological system to which oligonucleotides have an affinity from the remainder of the target molecules of the second biological system; and in step i), for at least one of the subsequent steps d) during the repetition of the combination of steps a) to h), only the target molecule (s) of said second biological system that have been separated in step h') are used as target molecule(s) of said second biological system.

It is also an object of this invention to provide a method comprising the steps of;

a) contacting a pool of oligonucleotides with target molecules of a first biological system, wherein some of the oligonucleotides from said pool may have an affinity for one or more of the target molecules of said first biological system;

b) removing the oligonucleotides having an affinity for the one or more of the target molecules of the second biological system;

c) amplifying the remaining oligonucleotides, to yield a pool enriched in oligonucleotides having a lower affinity for the target molecules of the first biological system;

d) contacting the amplified oligonucleotides of step c) with target molecules of a second biological system, wherein some of said oligonucleotides have an affinity for at least one of the target molecules of the second biological system;

e) separating the oligonucleotides having an affinity for the at least one target molecule from the remainder of the pool;

f) amplifying the oligonucleotides which have been separated in step e), to yield a pool of oligonucleotides having a lower affinity for the target molecules of the first biological system and a higher affinity for the at least one target molecule of the second biological system; and g) repeating the combination of steps a) to f) until at least one difference is identified.

In a preferred embodiment, the above mentioned method is modified such that, in replacement of step g), the following steps are performed:

g) fractionating the amplified pool of step f) In at least two portions;

h) contacting a first pool's portion with target molecules of the second biological system and separating the at least one target molecule to which oligonucleotides have an affinity from the remainder of the target molecules; and i) repeating the combination of steps a) to h) until at least one difference is identified, wherein in at least one of the subsequent steps d):

a second pool's portion is used as the pool of oligonucleotides;

only the at least one target molecule separated in step h) is(are) used as target molecule(s) of said second biological system.

Preferably, step h) further comprises the sub-steps h') of contacting a third pool's portions with target molecules of the first biological system, and separating any target molecule to which oligonuclectides have an affinity from the remainder of the target molecules of said first biological system; and in step i), for at least one of the subsequent steps a) during the repetition of the combination of steps a) to h), only the target molecule(s) of the first biological system that have been separated in step h') are used as target molecule(s) of the first biological system.

Any of the aforesaid methods can be carried out in succession or in parallel.

Other objects and advantages of the present invention will be apparent from the following specification and the accompanying drawings which are for the purpose of illustration only.

DETAILED DESCRIPTION OF THE INVENTION

As stated herein before the method of the invention in named "STRIPGEN" for "Selective Technique for Rapid Identification of Proteins and GENes". The STRIPGEN method involves selection from a pool of oligonucleotide ligands having a higher affinity and specificity for target molecules of a first biological system and a lower affinity for binding target molecules of a second biological system (and vice versa). Once such oligonucleotides having been selected, a man skilled in the art may rapidly identify and isolate the target molecules.

One of the aspects of the STRIPGEN method is the fact that the identification of target molecules (proteins or other types of molecules) can be achieved without knowing the nature of the initial difference between the two biological systems under investigation. Another aspect is the fact that by using STRIPGEN, one can obtain specific ligands to a target molecule, even in the absence of a defined understanding of the involved epitope. The epitope is usually a substructural component of a larger macromolecule against which a selected oligonucleotide has affinity. An additional powerful feature of STRIPGEN lies in the simultaneous detection of target molecules and specific ligands that bind specifically and with a high affinity to targets molecules.

In its most basic form, the STRIPGEN method may be defined by the following steps:

1) A pool of oligonucleotides comprising a region of fixed sequence (i.e. each oligonucleotide contains the same sequence in the same location) and a region of randomized sequence, are contacted with target molecules from a first biological system under conditions favorable for binding. Some of the oligonucleotides of the pool having an affinity to the target molecules of the biological system will bind these molecules, thereby forming oligonucleotides-target complexes.

2) The oligonucleotides bound to the target molecules of the first biological system are separated from the remainder of the pool.

3) The bound oligonucleotides separated in 2) are then amplified to yield a pool enriched in oligonucleotides having a higher affinity and specificity for binding the target molecules of the first biological system.

4) The oligonucleotides amplified in the previous step are contacted with target molecules from a second biological system under conditions favorable for binding and the oligonucleotides which have an affinity to target molecules from the second biological system are removed.

5) The remaining oligonucleotides are amplified to yield a pool of oligonucleotides enriched in oligonucleotides having a higher affinity and specificity for binding target molecules of the first biological system but a lower affinity for binding target molecules of the second biological system.

6) These five steps are reiterated as many cycles as desired to identify at least one difference between the two biological systems. Ideally, these repetitive steps will yield oligonucleotides highly specific and having a high affinity in the binding of target molecules of the first biological system only.

Certain terms used to describe the invention herein are defined as follows:

As stated herein above, "STRIPGEN" methodology relate to the combination of iterative round of positive and negative selections over two biological systems in different states to obtain oligonucleotides (nucleic acids) which interact with target molecules from a first biological system in an adequate manner, but do not interact (or much less) to target molecules from a second biological system. An example of adequate interaction is binding to a protein. In the STRIPGEN method, repetitive steps of binding, separation and amplification allow to select, from a pool which contains a very large number of oligonucleotides, a small number, as low as only one, oligonucleotide which interact strongly with target molecules of a first biological system but not (or much less) with target molecules of a second biological system. Cycling of positive and negative selections are continued until at least one difference is identified. It will also appear as obvious to the man skilled in the art that the current method is "reversible" i.e. that the negative selection may precede the positive selection.

"Target molecules" relate to any compound to which an oligonucleotide may interact in a predetermined adequate manner. Any peptides, proteins, glycoproteins, hormones, receptors, antibodies, antigens, nucleic acids, carbohydrates, polysaccharides, lipids, pathogens, virus, chemical substances (such as a toxic substance), inhibitors, cofactors, substrates, growth factors, metabolites, analogs, drugs, dyes, nutrients, cells, tissues, etc., without limitation are includes as a potential STRIPGEN target molecules. Practically any molecules, chemical or biological, of any size can serve as STRIPGEN targets, including the target molecules that have been modified to increase the probability of an interaction between the target molecule and the oligonucleotide. The target molecules may also be fixed on a matrix. In the preferred embodiment, the target molecules are soluble proteins.

"Biological system" relate to any biological mixtures containing, or providing the STRIPGEN targets described above. This definition includes mixtures containing and/or deriving from biological fluids, a single cell, an aggregate of cells, a collection of cell types, an aggregate of macromolecules, a tissue, extracts and substructure isolation therefrom (cell membranes, cell nuclei, cell organelles), etc., without limitation. Any kind of cells may be used, including those subjected to numerous changes such as cycling (different cell cycles) transformation, transfection, activation, etc. The biological mixtures can be obtained from prokaryotes as well as eukaryotes, including human, animal, insect, plant, bacteria, yeast, fungus, etc.

"Oligonucleotides" means nucleic acid, either desoxyribonucleic acid (DNA), or ribonucleic acid (RNA), in single-stranded or double-stranded form and any chemical modifications thereof. Such modifications include, but are not limited to providing other chemical groups that incorporate additional charge, polarizability, hydrogen bonding or electrostatic interaction to one or more of nucleic acid bases of the oligonucleotide. Examples of modifications are, but are not limited to, modifying the bases such as substitution of 5-bromouracil, 5-position pyrimidine modifications, 8-position purine modifications, modifications at cytosine exocyclic amines, 2'-position sugar modifications, methylations, unusual base-pairing combinations such as the isobases isocytidine and isoguanidine, backbone modifications, 3' and 5' modifications such as capping, and the like, The modifications that occur after each round of amplification in a reversible or irreversible manner are also compatible with the current invention.

"Pool of oligonucleotides" is a mixture of nucleic acids of differing, randomized sequence. The pool of oligonucleotides may be prepared from naturally-occurring oligonucleotides or fragments thereof, from chemically synthesised oligonucleotides, from enzymatically synthesised oligonucleotides or oligonucleotides made by a combination of the foregoing techniques. In a preferred embodiment, to facilitate the amplification process, fixed sequences are surrounding a randomized region in each oligonucleotide. The length of the randomized region of the oligonucleotide is generally between 8 and 250 nucleotides, preferably between 15 and 60 nucleotides.

"Randomized region" means a segment of an oligonucleotide that can have any possible sequence over a given length. The length of the randomized region may be of various lengths, ranging from about fifteen to more than one hundred nucleotides. Randomized region also includes the random sequences deviating from mathematical ideality, since in certain occasion, a bias may be deliberately introduced during the synthesis of a randomized sequence. Reasons for introducing such bias are to affect the secondary structure of the oligonucleotide, to introduce bias toward specific molecules or to introduce certain structural characteristics. Among the techniques known by the person skilled in the art to introduce such bias, there is the alteration of the molar ratios of precursor nucleoside (or deoxynucleoside) triphosphates during the synthesis reaction and the alteration of the ratio of phosphoramidites during the chemical synthesis.

"An oligonucleotide having an affinity" is an oligonucleotide which interacts with a target molecule in a adequate manner. Examples of interaction with a target molecule in a adequate manner include, but are not limited to binding in a reversible manner to the target, catalytically changing the target, modifying or altering the target or its functional activity, binding covalently to the target, facilitating the reaction between the target and another molecule. In the preferred embodiment, this adequate manner is the reversible specific binding of oligonucleotides to a target molecule.

"Separating" means any process for partitioning or isolating the oligonucleotide having an affinity for target molecules from all the others oligonucleotides which are found in the pool. Separation can be done using many methods known in the art. Suitable examples of separating methods are equilibrium partitioning, filter binding, affinity chromatography, liquid-liquid partitioning, filtration, gel shift, and density gradient centrifugation. Since the target molecules of the present invention may be soluble or non-soluble, there are numerous simple, well suited partitioning methods which may be used according to the principle of the current invention. In the illustrated preferred embodiments, a gel shift method is used. The person skilled in the art will base its choice of separating method depending on the properties of the target molecules and of the oligonucleotide.

"Amplifying" means any process that increases the number of copies of a molecule or class of molecules. According to the method of the invention, an amplification step follows each step in which oligonucleotides are separated. In the steps of positive selection, only the oligonucleotides associated with a desirable target molecules are amplified. To the opposite, during the negative selection steps, only the oligonucleotides not associated with a target molecules are amplified. The man skilled in the art will know, depending of the type of oligonucleotides used during the selections, which method and conditions to use for amplifying the desired oligonucleotides. As a non-restrictive example, amplifying RNA molecules can be carried out by a sequence of three reactions: making cDNA copies of selected RNAs, using the polymerase chain reaction to increase the copy number of each CDNA, and transcribing the cDNA copies to obtain RNA molecules having the same sequences as the selected RNAs. Those skilled in the art know many other reactions that can be used, including direct DNA replication and direct RNA amplification. Ideally, the amplified mixture should be representative of the proportions of the different oligonucleotides in the mixture prior to amplification.

It is evident that the STRIPGEN method has several advantages. It is applicable to any simple or complex biological systems containing a mixture of target molecules to which oligonucleotides may have an affinity and form oligonucleotides-target complex. If there are qualitative or quantitative differences in the target molecules from two biological systems, the oligonucleotides forming oligonucleotides-target complex may be isolated, identified and used for:

1) identification of the differences among a plurality of biological systems;
2) purification of an unknown target molecule which is present in one, but not in the other(s) system(s); and/or
3) understanding of the activity of the target which is unique to a particular system (apoptosis, differentiation, proliferation, cell cycling, etc.) And modulation of this activity.

It is important to note that iterative rounds of only positive (classical) selection over just one complex system do not produce oligonucleotides, which can be used for previously mentioned purposes 1 to 3. However, oligonucleotides selected in the classical mode would give higher binding constants for a given complex mixtures (A or B).

In the STRIPGEN method, the iterative rounds of positive and negative selections are designed not to give the best oligonucleotides binding to target molecules from a first and/or second biological system, but to give the oligonucleotides which are binding to the target molecules of a first system, but not (or with much less affinity) to the target molecules of the other system. Therefore, in the STRIPGEN method, the selection criterion is difference in binding affinities, but not the absolute winner in binding affinity. Furthermore, as stated previously, the STRIPGEN method is "reversible" since that the negative selection may precede the positive selection.

Oligonucleotides selected according to the STRIPGEN method can prove to be highly selective and effective diagnostic and therapeutic tools in a variety of areas (genetic defects, infectious diseases, cancer) as it will be described in detail herein after. This technical approach to drug discovery combines the strong advantage of eliminating the need to know the tridimensional structure of the target molecule or its ligand.

STRIPGEN provides the ability to discriminate between closely related but different cells and tissue types. The positive/negative selection steps can be done against a similar cell line or cell type, different cells, pathological vs normal tissues, cellular extracts therefrom, non-specific antibody or other available targets, body fluids (plasma, blood, urine, etc.), or any two systems (or more than two) with one or many differences. STRIPGEN could also be applied to the same biological system present in two (or more) different states. STRIPGEN could be applied not only to humans, but also to all living organisms. Using the STRIPGEN method, it is thus possible to select oligonucleotides able to recognise the differences between normal and abnormal tissue and cells of a particular type. For example, the STRIPGEN method may select oligonucleotides that recognise precisely a single or many difference(s) between a cancerous cell and an untransformed cell of the same tissue type. As exemplified in detail herein later, a positive selection is first performed against a nuclear protein extracts of induce human cancer cells, then a negative selection is performed against a similar nuclear protein extracts of the same non-induced human cancer cells. Oligonucleotides ligands that interact with targets from both induced and non-induced extracts will be removed by the negative selection and only those oligonucleotides ligands that specifically bind the protein extracts of induce cells will be identified (or retained). The resulting oligonucleotides ligands would be specific for nuclear proteins associated with tumors.

Once highly specific oligonucleotides are obtained it becomes possible to identify the difference(s), and eventually purify and characterise it (them). The new target molecule can be a previously unknown protein or peptide, lipid, carbohydrate, etc. Virtually any molecule can be identified by the STRIPGEN method.

The methods for purifying new macromolecules are well-known for the man skilled in the art, especially in the art of protein purification. Many usable methods are described in detail in Marshak, D. R. et al. (1996) *Strategies for Protein Purification and Characterization*, A Laboratory Course Manual, Cold Spring Harbor Laboratory Press. Among the well-known standard purification methods there are gel chromatography, affinity chromatography, ultrafiltration, electrophoresis. A typical example would be to load a mixture of soluble target molecules on a column wherein the beads are covalently coated with high-affinity oligonucleotide to isolate the target molecules from the mixture, on the basis of the affinity of the oligonucleotides and the target.

Once a protein has been purified it is possible to determine its sequence using peptide microsequencing, Edman sequencing, etc. Determination of the amino acid sequence of a portion of the protein will lead to the identification of the gene that encodes for that protein. This could be done through a search in the public cDNA libraries or the direct cloning of the gene.

The oligonucleotides selected by the STRIPGEN method are also useful as diagnostic and therapeutic reagents and can be used both in vitro and in vivo. The oligonucleotides generated by STRIPGEN are particularly suited for diagnostic application since they can bind target molecules with a high affinity and with a high specificity. These characteristics are the desired properties one skilled in the art would seek for a diagnostic ligand. For example, oligonucleotide ligands that bind specifically to a pathological tissue, such as human tumors, may have a role in imaging pathological conditions. The oligonucleotides generated by STRIPGEN may thus be routinely adapted for diagnostic purposes according to any number of techniques employed by those skilled in the art.

The oligonucleotide ligands to tissue targets or newly identified macromolecule components are also useful for the treatment or prevention of diseases or medical conditions in human or animal. The oligonucleotide can bind to receptors and be useful as receptor agonist or antagonist and even for the therapeutic delivery of cytotoxic compounds or immune enhancing substances. Details regarding these applications are well-known to the ones skilled in the art.

1-Schematic Example of the STRIPGEN Method

Figure 1:
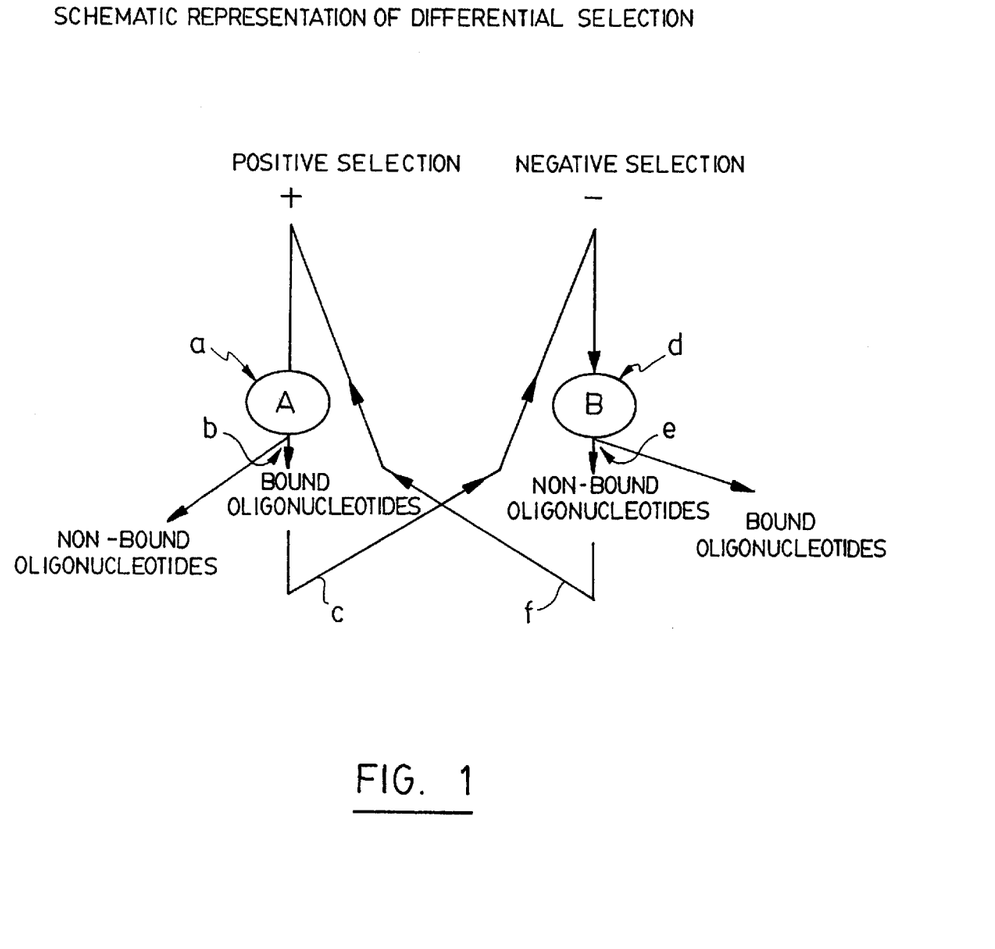
FIG. 1 is a schematic representation of the STRIPGEN method showing an example of positive selection over a first biological system (system A) and negative selection over a second biological system (system B).

FIG. 1 is a schematic representation of the STRIPGEN method. In this particular example, only the oligonucleotides which bind to the targets of a first biological system (system A), but which do not bind to the targets of a second biological system (system B) are of interest. Thus, it is performed a positive selection over a system A and a negative selection over a system B. This will yield oligonucleotides which bind to targets which are present in system A but absent (or less prevalent) from system B. The targets could be proteins which are present only in the system A, or in a relative higher level, as compared to the system B.

A pool of oligonucleotide ligands is first prepared. STRIPGEN can be carried out either with a pool of synthetic single strand or double strand DNA ligands (DNA STRIPGEN) or with a pool of RNA ligands (RNA STRIPGEN). DNA ligands can serve as transcription templated to generate the RNA ligands (see below for details).

In all cases, the oligonucleotide ligands include regions of fixed sequences (i.e. each of the oligonucleotide of the pool contains the same sequences in the same location) and regions of randomized sequences. The fixed regions are preferably selected to allow (a) primer annealing for complementary DNA (cDNA) synthesis when the selected oligonucleotides are RNA, (b) polymerase chain reaction (PCR) amplification to increase the copy number of each cDNA, and (c) efficient T7 RNA polymerase transcription of cDNA copies to obtain RNA molecules having the same sequences as the selected RNA molecules. The fixed regions are preferably 15 to 20 nucleotides in length and located at each end of the oligonucleotide. The above given examples of fixed regions that may be used are not restrictive since the man skilled in the art will be able to select fixed regions that will answer his need.

The randomized sequences can be totally randomized (i.e. the probability of finding a base at any position being one of four) or partially randomized (e.g. the probability of finding a base at any location can be selected at any level between 0 and 100 percent). Preferably the size of the random region varies from 15 to 60 nucleotides. For example, preparation of random sequences can be achieved by the addition of a freshly prepared equimolar mixture of all four deoxynucleotide phosphoramidites by automated solid-phase synthesis according to the manufacturer's protocol on an Applied Biosystems ABI 394 instrument at a 1 $\mu$mol scale. After synthesis, DNA is purified by gel electrophoresis. DNA generated from solid-phase synthesis can be used for the first round of STRIPGEN process, provided that it has been completely deprotected and gel purified. Detailed examples of the preparation of appropriate oligonucleotide ligands are given in Methods in Enzymology, Section V, volume 267: p.275 (1996).

DNA generated from solid-phase synthesis can be used for the first round of STRIPGEN process, provided that it has been completely deprotected and gel purified.

Single-stranded DNA (ssDNA) for DNA STRIPGEN Protocol

To use as DNA, DNA generated from solid-phase synthesis can be used for the first round of STRIPGEN process, provided that it has been completely deprotected and gel purified. For subsequent rounds of DNA STRIPGEN, ssDNA is prepared from the Polymerase chain reaction (PCR) amplification products. PCR amplification utilizes a biotinylated 3' primer such that the PCR double-strand DNA (dsDNA) products contain one biotinylated strand. The biotinylated DNA strand can be readily separated from the non-biotinylated DNA strand as follows: PCR-amplified dsDNA with one biotinylated DNA strand is resuspended with streptavidin and the reaction mixture is denatured and electrophoresed on a denaturing polyacrylamide gel. The streptavidin/biotin strand will migrate near the top of the gel, whereas the non-biotinylated DNA strand will migrate at lower position far from the top of the gel. Full-length ssDNA is identified by autoradiography or UV shadow and is eluted from the gel slice.

Conversion of the single-stranded synthetic DNA pool to a double-stranded (ds) DNA pool utilizes either PCR amplification or elongation of a primer complementary to the 3' fixed region by the klenow fragment of DNA polymerase that lacks exonuclease activity. The 5' primer complementary to the 3' fixed region contains the T7 RNA polymerase promoter and the 5' fixed region. The primer is annealed to the synthetic ssDNA template, and the dsDNA template is generated by a klenow fragment fill-in reaction at the 3'-termini.

RNA for RNA STRIPGEN Protocol

In certain cases, it may be preferable to use RNA as oligonucleotides. Being single strand, RNA is more flexible than dsDNA. RNA may thus forms various structures that are not possible to obtain with dsDNA. RNA is however more sensitive to degradation than DNA. To generate the random sequence RNA required for the first round of selection, a large scale transcription reaction is set up. It is known that RNA generated with 2'-aminopyrimidines or 2'-fluoro-pyrimidines is resistant to pyrimidinespecific endonucleases. In a typical selection experiment, the RNA is radiolabelled in each round with radioactive alpha ATP. The RNA recovered from the first round of selection is annealed to a primer and reverse transcribed into cDNA with avian myeloblastosis virus (AMV) reverse transcriptase (RT). The cDNA is converted into double-stranded transcription templates by PCR amplification. As for the first round of selection, the generated dsDNA is used to generate RNA molecules for the second round of selection.

Identification of Target Molecules Present in System A but not in System B

Referring more specifically to FIG. 1, in step a), a pool of oligonucleotide ligands is contacted with selected targets of a first biological system (A) under conditions favorable for binding between the targets and the members of the oligonucleotides pool. Generally, the oligonucleotides ligands are present in molar excess over the target mixture. Under these conditions, the interactions between the targets and the oligonucleotide nucleic acids (ligands) can be considered as forming nucleic acid-target pairs between the target and those nucleic acids having the strongest affinity for the target.

In step b), the oligonucleotides with the highest affinity for the targets of system A (i.e. those bound to these targets) are separated from the oligonucleotides with lesser affinity to the target (i.e. unbound oligonucleotides). The separation process can be accomplished by various procedures as described herein before (see also Methods in Enzymology, Section V, volume 267: p.275 (1996).

In step c), the oligonucleotides selected as having the relatively higher affinity to the target of system A and separated in step b) are then amplified by PCR to create a new oligonucleotides pool that is enriched in nucleic acids that have a relatively higher affinity for the targets of the first system (system A). These new positively selected and amplified oligonucleotides are named "A+".

Steps a) to c) are thus named "positive selection" since only the oligonucleotides with the highest affinity for the targets of system A are selected and amplified.

In step d), the amplified oligonucleotides of step c) are contacted with a second biological system (B) under conditions favorable for binding between the target and the members of the oligonucleotides pool. These conditions are described below. Once again, nucleic acid-target pairs interactions are formed between the target and the nucleic acids having the strongest affinity for the target.

In step e), the oligonucleotides not bound to the second biological system (system B) are separated from the bound oligonucleotides.

In step f), the oligonucleotides selected during the partitioning of step e) as having the relatively lower affinity to the targets of system B are then amplified to create a new oligonucleotides pool that is enriched in nucleic acids having a relatively lower affinity to the targets of the second system (system B). In fact, since these newly negatively selected oligonucleotides have been previously positively selected against system A [steps a) to c)], the newly amplified oligonucleotides pool is named "A+B−".

Step d) to f) is thus named "negative selection" since the oligonucleotides not bound to the targets of the second biological system are separated from the bound oligonucleotides.

The critical factor for the rounds of negative selection, is the amount of oligonucleotides which are removed during this step. In positive rounds of selection, the oligonucleotide ligands should be present in molar excess over the target mixture to make sure that binding occurs and detected. However, during the negative selection the ratio should be inversed since it is the absence of binding which is preferred. Generally an empirical approach is taken in order to find the best molar ratio between oligonucleotides and the targets mixture. To do so, in each contacting step, various target mixtures and oligonucleotide concentrations should be tried in order to find the best molar ratio between oligonucleotides and target mixtures. The man skilled in the art will base the final decision depending on the complexity and the nature of the differences between systems A and B, and depending on the results obtained in each particular case. See FIG. 2 for an example of a negative selection after one round of positive selection.

By repeating the six contacting, partitioning and amplifying steps described above, i.e. using the amplified negatively selected oligonucleotides of step f) for contacting with the targets mixture of the first biological system (A), the newly formed oligonucleotide pool contains fewer and fewer unique sequences. At each round, the average degree of affinity of the nucleic acids to the targets of system A will increase whereas the affinity of the nucleic acids to the targets of system B will decrease. Taken to its extreme, the STRIPGEN method will yield an oligonucleotides pool containing one or a small number of nucleic acids representing those nucleic acids from the original mixtures having the highest affinity to the target molecules of system A but the lowest affinity to the target molecules of system B.

2- STRIPGEN II

The STRIPGEN method as described above could be in certain cases limited by the product of the oligonucleotide affinity (kd) toward the target protein and the concentration of the protein [p]. Such product is defined as (kd)×[p].

As an hypothetical example, there is a protein "p1" present at very low concentration [p1] in system A but absent from system B. Such protein is a target for the pool of oligonucleotide ligands used in the method. However, the protein p1 has a affinity (kd1) which is very low for these ligands as compared to another protein "p2" which has a high affinity (kd2) for these ligands. "P2" is present in a high concentration [p2] in system A but is absent from system B. Thus, it will be very difficult to isolate the oligonucleotides bound to protein "p1" since the lower affinity of nucleic acid ligands for protein "p1" as compared to "p2" and the low concentration of this protein, will lead to elimination of oligonucleotides binding to protein "p1" during the rounds of selection. On the other hand, oligonucleotides will have access to the predominant protein "p2" and thus only these oligonucleotides will be preferentially amplified during the selection process. The repetitive contacting, partitioning and amplifying steps will thus yield a pool enriched only in oligonucleotides specific to protein "p2".

Figure 5:
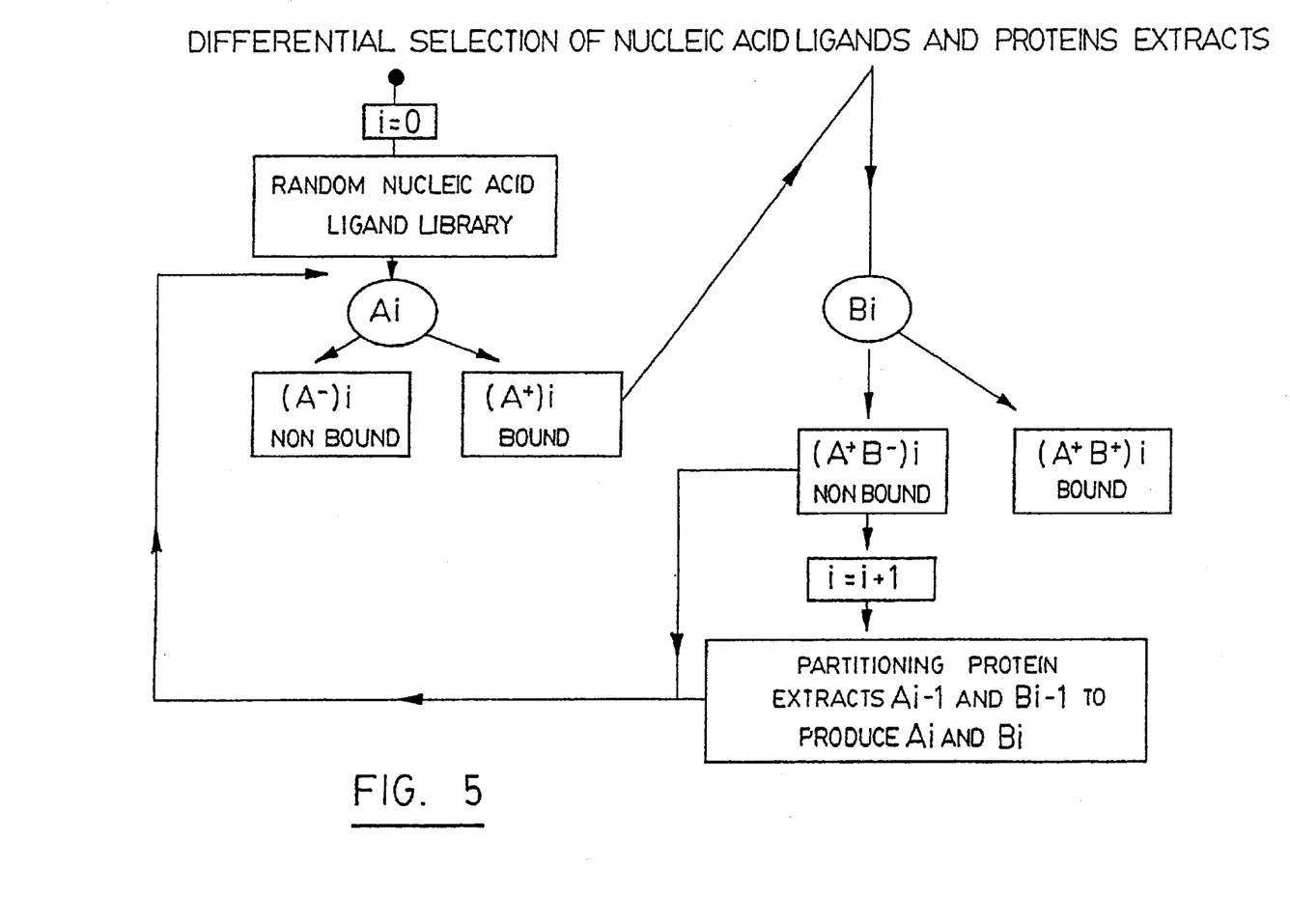
FIG. 5 is a schematic representation of another embodiment of the method of the Invention named "STRIPGEN II".

To resolve the above problem, the Applicant proposes in another embodiment of the invention, another method in which the standard STRIPGEN method is enhanced. The improved method is called "STRIPGEN II". As a base, STRIPGEN II uses the same repetitive steps a) to f) described in the standard STRIPGEN. However, the main difference, is the modification of step b) which involves the fractionation of protein extracts. As shown on FIG. 5, the "A+B-" oligonucleotides are first used for separating the protein extracts Ai and Bi into subfractions denoted i+1. "i" refer to the number of the current step. "i" equal 0 refers to the original protein extracts. Similarly the selected oligonucleotides corresponding to the protein extract subfraction will bear the same index i as the protein subfractions. For example protein extract A0 and B0 are contacted with (A+B-)0 oligonucleotides. The partitioning of bound proteins from non-bound proteins produces new protein extracts A1 and B1, and so on (FIG. 5). A person skilled in the art will however understand that to produce the extract Bi+1 with the oligonucleotides that do not bind to extract Bi, one must use higher concentration of extract Bi. It is also possible to use this method by partitioning only extract A and by keeping extract B constant.

Figure 6:
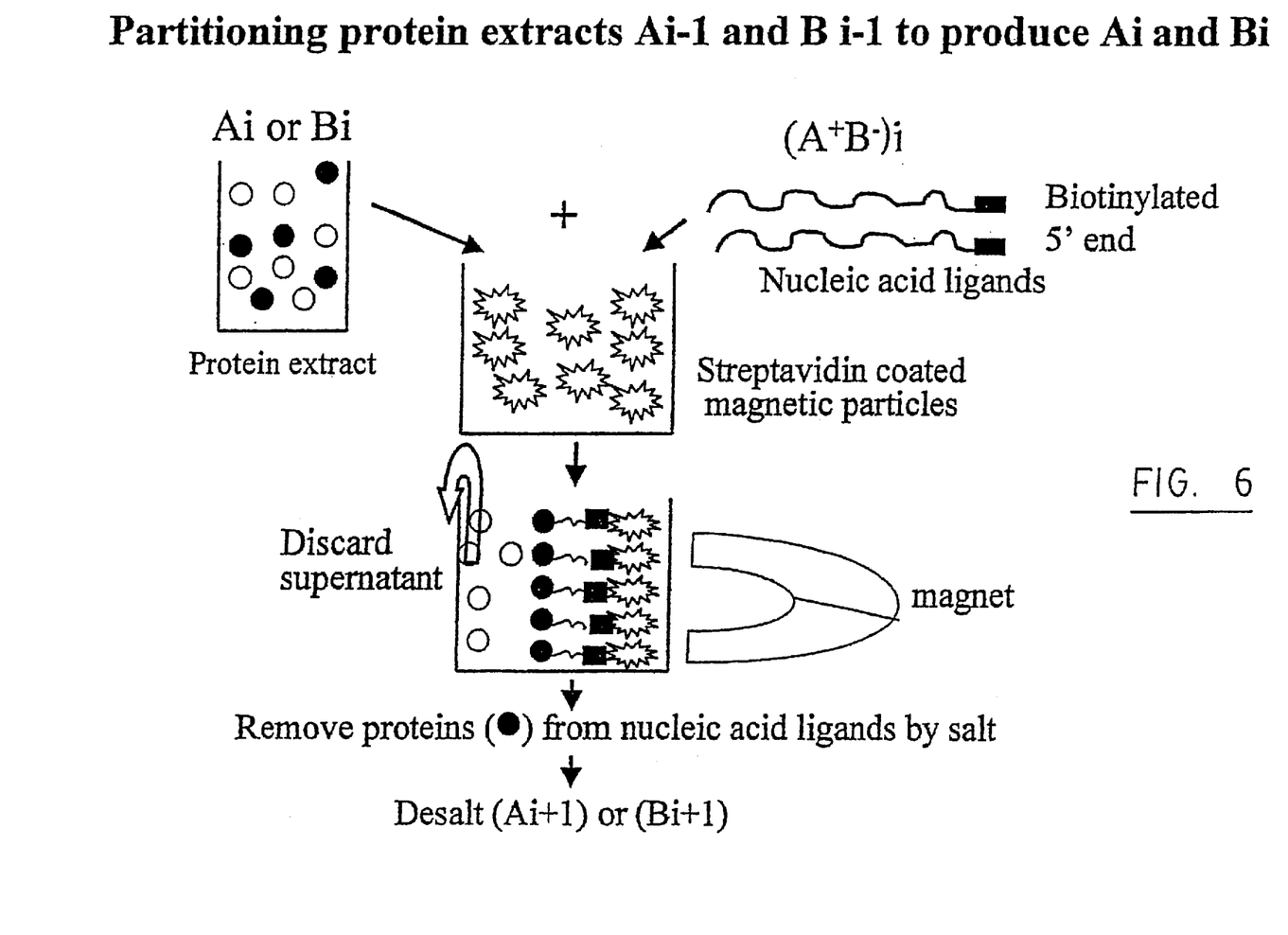
FIG. 6 is a schematic representation of an example of protein-partitioning procedure that could be use according to the STRIPGEN II method.

FIG. 6 illustrates an example of protein-partitioning procedure that could be used. In this example the (A+B-)i oligonucleotides are 5'-end labelled with biotin and streptavidin magnetic particles are used for partitioning. The components of protein extract A0 and B0 to which are bound oligonucleotides (A+B-) 0 are separated from the proteins to which no oligonucleotides are bound. After discarding the unbound proteins, the bound proteins named A1 and B1 are separated from oligonucleotides by using high salt concentration. The A1 and B1 proteins are desalted and these extracts are used for the second round of positive/negative selections (see FIG. 5).

Although in this example both protein extracts A and B were fractionated, it is also possible to subfractionate only extract A, producing new extracts Al, A2 . . . An . . . , and keep the original extract B intact. The advantage of fractionating only extract A but not extract B, is that less manipulation is required to find differences between A and B. However, the simultaneous fractionation of both extracts A and B is more sensitive, since the differences between system A and system B will be identified even if the differentially expressed proteins exist in extremely small concentration and/or have very low affinity to the oligonucleotide ligands.

3-Identification of Target Molecules Present in System B but not in System A

Since the current methods are "reversible", identification of target molecules expressed in system B but not in system A can be done almost exactly as described in experiments (1) and/or (2). However, in this case the first round consists of a first step of positive selection against system B (yielding to B+ oligonucleotides), followed by a second step of negative selection against system A (yielding to B+A- oligonucleotides). The positive/negative selections are repeated until a difference is seen.

Another option is to do a first step of negative selection against system A (yielding to A- oligonucleotides), followed by a second step of positive selection against system B (yielding to A-B+ oligonucleotides). The negative/positive selections are repeated until a difference is seen.

4-Simultaneous Identification of Proteins that are Differentially Expressed in System A and System B The experiments described in (1), (2) and/or (3) can be done in parallel for the simultaneous identification of proteins that are differentially expressed in system A and system B.

5- Identification of the Oligonucleotides Ligands and Targets Molecules to which Oligonucleotides Bind As stated herein before, oligonucleotide ligands that are specific to targets molecules from either system may be identified. These oligonucleotides will then be very useful as tools to purify the protein components of the studied biological system. As a non-restrictive example, these oligonucleotides may be amplified by PCR and can be cloned by using the TA-cloning kit. The advantage of using TA-cloning is that PCR products can be directly cloned without further processing. The sequencing of the cloned ligand can be done by current procedures.

Proteins identified either from system A or system B can be purified by using their specific ligands. The methods of protein purification are well-known to the one skilled in the art. One way to purify ligand-specific proteins is by DNA affinity chromatography (see Marshak, D. R. et al. (1996) Strategies for Protein Purification and Characterization, A Laboratory Course Manual, Cold Spring Harbor Laboratory Press. This procedure begins with immobilizing DNA ligands to commercially available cyanogen Bromide (CNBr)-activated Sepharose.

A partial amino acid sequence of the purified protein can be determined by current procedures such as the Edman-degradation reaction or other techniques know to the man skilled in the art. The partial amino acids sequence of the protein can then be used to deduce the DNA sequence of the encoding gene. The gene may also be cloned. The DNA sequence can be used to identify the gene either by cloning from commercially available cDNA or genomic libraries or through public gene banks. The details regarding these applications are wellknown to the ones skilled in the art.

The following non-limiting examples illustrate results obtained according to the method of the current invention.

EXAMPLE 1

Differential Binding Ability of Oligonucleotides-target Mixtures at Different Stages of the STRIPGEN Method The STRIPGEN method was used to compare gene expression at the protein level between two human cell extracts. The two nuclear protein extracts were from K562 human cancer cell line (chronic myelogenous leukemia) induced with phorbol ester (protein extract A) and non-induced (protein extract B). The two extracts were purchased from Santa Cruz Biotechnology Inc. And prepared according to the method of Dignam et al, (1983) *Nucl. Acids Res.* 11: 1415.

Double strand DNA oligonucleotides having a fifteen nucleotides random core were used as ligands. The left and right arms fixed regions of the ligands used for PCR amplification were respectively 5'-GTGGACTAAGGCATTGCCAG-3' (SEQ ID NO: 1) and 5'-TGGCTAGCTTCCAGGTCTAT-3' (SEQ ID NO: 2). Construction of the double strand DNA STRIPGEN library was done according to procedures described in Methods in Enzymology, Section V, volume 267: p. 275 (1996). DNA manipulation (gel extraction, phenol/chloroform purification, DNA precipitation, 5'-end labelling of DNA) were done according to standard procedures which are completely described in Molecular cloning: A laboratory manual, Maniatis et al., 1988.

The first round of STRIPGEN method comprises first a positive selection followed by a negative selection. To promote the binding of oligonucleotides to the target molecules, the oligonucleotides are preferably present in molar excess over the targets during the positive rounds of selection, for example, 1–10 pmols of oligonucleotides versus 0.2 µg of proteins extracts. In the present case, 1–10 pmol of $p^{32}$-5' end labelled oligonucleotide ligands (20 000–50 000 cpm) were mixed with 0.2 µg of nuclear-protein extracts A or B in the presence of 1 µg of salmon sperm DNA in gel-shift binding buffer (50 mM tris-HCl, pH 8.3, 60 mM NaCl, 10 mM $MgCl_2$) and incubated for 20 to 30 min on ice. Typically, reactions were done in 20–50 µl volumes. The mixtures obtained were then subjected to a gel mobility shift assay, also known as gel retardation assay or electrophoretic mobility-shift assay (EMSA). Since the resulting protein-ligand complex has a significantly lower mobility in the gel than that the free oligonucleotides, it is therefore possible to separate the bound oligonucleotide ligands from the non-bound ones. In the present example, the samples were loaded and run on an 8% non-denaturing polyacrylamide gel. The results were visualised by autoradiography (Kodak X-OMAT film).

The less mobile oligonucleotide ligands bound to protein from extract A or B were cut from the gel and amplified by PCR. PCR reactions were done under following conditions: 10 µl of 10×PCR buffer, 7 mM $MgCl_2$, 1 mM dNTP, 2 µM primers and 5–10 units of Taq DNA polymerase in a total volume of 100 µl. The temperature cycle was 95° C. (30 sec), 60° C. (30 sec) and 72° C. (30 sec). The cycle was repeated between 15 and 20 times, dependent of the status of PCR product (after 15 cycles the DNA was tested on small non-denaturing polyacrylamide gels and, if necessary, the PCR was continued for next 5 cycles). The primers were selected to have a complementary sequence to the fixed ends region of the oligonucleotides. The new positively selected and amplified oligonucleotide ligands for system A were named "A+", and those positively selected for system B were named "B+".

The A+ oligonucleotides were used for a negative selection against protein extract B and the B+oligonucleotides were used for a negative selection against protein extract A. In negative rounds of selection, the ratio of proteins/DNA is preferably much bigger than in positive selection (for example 0.1 pmol of DNA versus 2–5 µg of protein extract). In the current example, empirical titration experiment was done before each round of negative selection, to find the best molar ratio between oligonucleotides and target mixtures, in order to remove 30–60% of oligonucleotides bound to protein extract.

The A+ and B+ oligonucleotides were $p^{32}$-5' end labelled and 0.1 pmol of these oligonucleotides (20 000–50 000 cpm) were mixed with 2–5 µg of nuclear protein extract B (A+ oligonucleotides) or A (B+ oligonucleotides) in the presence of 1 µg of salmon sperm DNA in gel-shift binding buffer and incubated for 20 to 30 min on ice. Typically reactions were done in 20–50 µl volumes. The mixtures obtained were loaded on 8% non-denaturing polyacrilamide gels. The results were visualised by autoradiography and are shown in FIG. 2.

Figure 2:
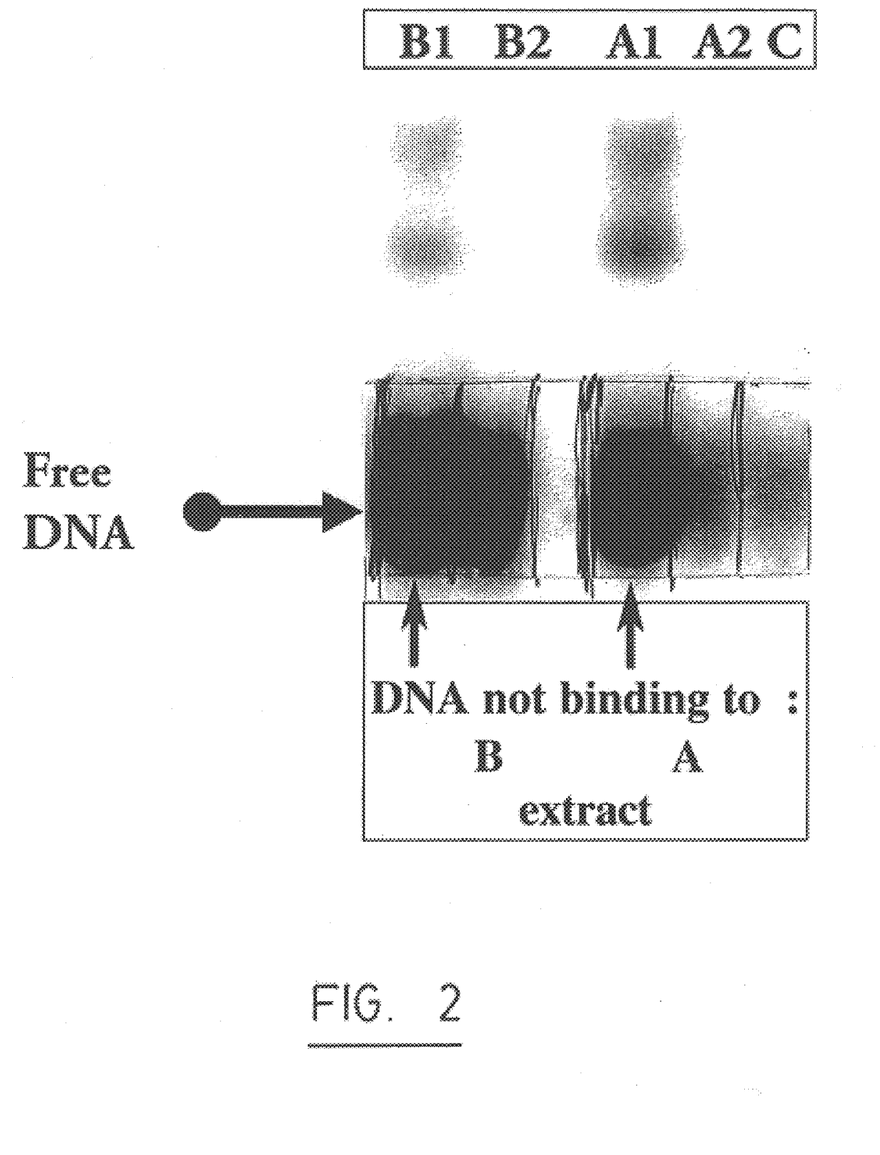
FIG. 2 is an autoradiography of a polyacrylamide gel showing various oligonucleotides-protein mixtures in an example of negative selection done after a first round of positive selection. The unbound oligonucleotides indicated with an arrow were used for the next round of PCR amplification and the next cycle of positive/negative selection. Legend: B1: protein extract B, 2 $\mu$g+DNA positively selected with A; B2: protein extract B, 0.2 $\mu$g+DNA positively selected with A; A1, protein extract A, 2 $\mu$g+DNA positively selected with B; A2: protein extract A, 0.2 $\mu$g+DNA positively selected with E; C: Free DNA (no protein extract): 1 pmol.

The tracks numbered B1 and B2 on FIG. 2 illustrate the results obtained with respectively 2 µg and 0.02 µg of protein extract B using the A+ oligonucleotides during the incubation step. As shown, two bands representing the A+ oligonucleotides bound to proteins from the extract B were detected in the sample containing 2 µg of protein extract B during the incubation (track B1). The intensities of unbound oligonucleotides (indicated on the figures by the arrow "free DNA") were calculated to represent about30–60% on the total oligonucleotides in the track. In track B2, no bound oligonucleotides were detected. The intensities of unbound nucleotides in track B2 thus represent nearly 100% of the total oligonucleotides loaded on the gel. Similarly the tracks numbered A1 and A2 on FIG. 2 illustrate the results obtained with respectively 2 µg and 0.02 µg of protein extract A using the B+ oligonucleotides during the incubation step. Two bands representing the B+ oligonucleotides bound to proteins from the extract A were detected.

For the next round, the unbound oligonucleotides of track B1 (indicated on the figures by the arrow "free DNA") were cut from the gel and amplified using the same method and conditions described above. These previously positively selected and newly negatively selected and amplified oligonucleotides ligands were named "A+B−" oligonucleotides.

Two µg of protein extract A were digested with proteinase K in order to cut in part the proteins. The digested extract was recovered following a phenol-chloroform extraction and incubated as described above with the A+B− oligonucleotides. As shown on lane C of FIG. 2, no binding was detected, confirming the 3-dimensional specificity of the A+B− oligonucleotides for proteins from extract A.

EXAMPLE 2

Differential Binding Ability of Oligonucleotides-target Mixtures at Different Stages of the STRIPGEN Method As stated above, in the positive rounds of selection of the STRIPGEN method the oligonucleotides are preferably used in a molar excess over protein extract A (usually we use 1 to 10 pmoles of oligonucleotides versus 0.2 ug of protein extract A). In contrast, during the negative rounds of selection, the ratio of protein extract B/oligonucleotides is preferably much higher relative to that used during positive selection (usually 0.1 pmole of oligonucleotides versus 2 to 5 ug of protein extract B). The Applicant found that a method including a negative selection immediately after the positive selection, without amplification, as suggested in U.S. Pat. No. 5,712,375 is not effective since that, after the first round of positive selection, the partitioned oligonucleotides with high affinity to extract A bind totally to extract B during the first round of negative selection. It is only when the amount of extract B was decreased that the Applicant was able to find oligonucleotides that do not bind to extract B. However, amplification of these unbound oligonucleotides leads to a mixture of oligonucleotides that are not specific to extract A since they still bind to extract A and extract B when both extracts were used in equal amount in the second round of positive and negative selections (see FIG. 3. lanes 4 and 5). Thus, without amplification of oligonucleotides after partitioning and repeating the cycles of positive and negative selections, the difference between extract A and extract B could not be found.

Figure 3:
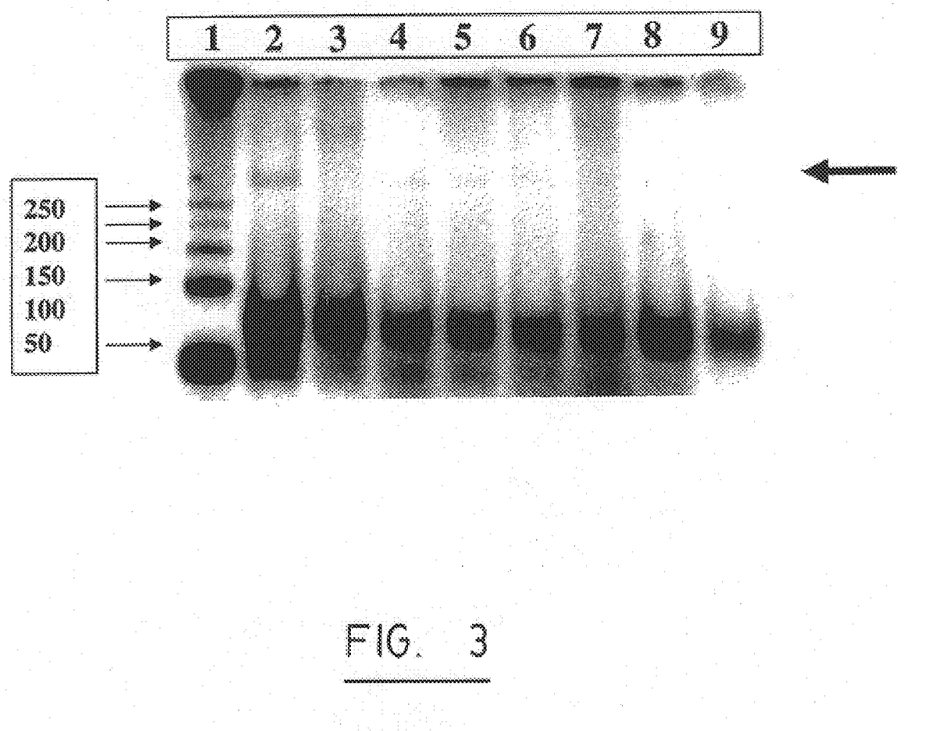
FIG. 3 is an autoradiography of a polyacrylamide gel showing oligonucleotides-protein mixtures at various stages of positive and negative selections. The positive selections for nuclear proteins present in extract A versus B produced the differential pattern in gel-shift assay. Legend: line 1: 50 base pair Marker (NEB): line 2: Complex between DNA and extract A, after three rounds of positive/negative selection for extract A, against extract B; line 3: Complex between DNA and extract B. After three rounds of positive/negative selection for extract A, but against extract B; Line 4: Complex between DNA and extract A, after one round of positive selection for extract A but negative for B; Line 5: Complex between DNA and extract B, after one round of positive selection for extract A; but against extract B; This shows that one round of positive/negative selection is not enough to discriminate between extract A and extract B; Line 6: Complex between DNA and extract A, after four rounds of positive/negative selection for extract, A, against extract B: Line 7: Complex between DNA and extract B, after three rounds of positive/negative selection for extract A, against extract B; Line 8: Complex between DNA and extract B, after three rounds of positive/negative selection for extract B, against extract A; Line 9: Complex between DNA and extract A, after three rounds of positive/negative selection for extract B, against extract A

To resolve that problem of sensitivity and specificity, the Applicant has discovered that amplification of the partitioned oligonucleotides during each of the rounds of positive and negative selections are essential to find the differences between a first biological system (such as extract A) and a second biological system (such as extract B). As shown in FIG. 3 (lanes 2 and 3, 6 and 7), a differential pattern of oligonucleotide-protein complexes starts to emerge after the third round of positive/negative selections. The oligonucleotide-protein complexes are visible only in the presence of extract A, giving a significantly stronger signal (lanes 2 and 6), than in the presence of extract B (lanes 3 and 7). Similarly, the oligonucleotide-protein complexes obtained after positive selection for extract B (negatively selected against protein extract A) are visible only in the presence of extract B (lane 8) but not with protein extract A (lane 9). Although that both STRIPGEN selection procedures (A versus B and B versus A) produced oligonucleotide-protein complexes with a similar mobility in the gel, these complexes are of different nature. As shown in FIG. 3, the oligonucleotides positively selected against A produce a differential pattern when incubated with extract A (lane 2) and extract B (lane 3). The same is also true for oligonucleotides positively selected against B and incubated with extract B (lane 8) and extract A (lane 9).

EXAMPLE 3

Results After Nine Repetitive Rounds of the STRIPGEN Method

Figure 4:
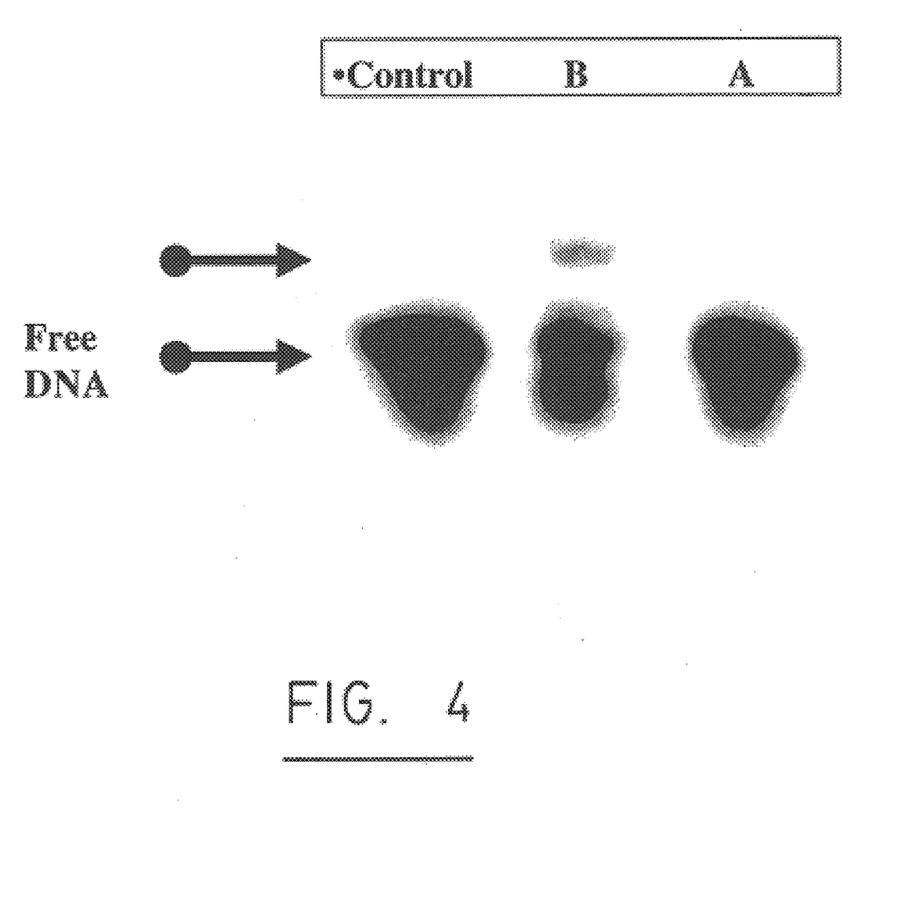
FIG. 4 is an autoradiography of a polyacrylamide gel showing oligonucleotides-protein mixtures after nine rounds of repetitive positive selection over a protein extract A and negative selection over a protein extract B. Lane A: 0.1 $\mu$g of nuclear extracts A added during the incubation; Lane B: 0.1 $\mu$g of nuclear extracts B added during the incubation. The control line (Control) contains only the oligonucleotide obtained after the ninth round of StripGen selection procedure.

FIG. 4 illustrates nine rounds of repetitive positive selection against extract A and negative selection against extract B. The positive/negative selections were performed as described herein before. The late selected A+B− oligonucleotides were then incubated with 0.1 µg of nuclear extract A (lane A) or with 0.1 µg of nuclear extract B (lane B). As shown on the autoradiogram, the band pointed up by the upper arrow shows that the late rounds of A+B− selected oligonucleotides have a high affinity and specificity only for protein(s) from the extract A but not to proteins from the extract B since oligonucleotide-protein complexes are seen only with extract A (lane A) but not with extract B (lane B).

This differential pattern obtained after the ninth round of positive/negative selections is also much stronger as compared with only three rounds (lanes 2–3, FIG. 3).

The invention disclosed herein is not limited in scope to the embodiments disclosed herein. As disclosed, the method of the invention may be applied by those skilled in the art to produce a large number of oligonucleotides. Appropriate modifications, adaptations and expedients for applying the teaching herein in individual cases can be employed and understood by those skilled in the art, within the scope of the invention as disclosed and claimed herein.

---

---

What is claimed is:

1. A method for selecting oligonucleotides able of identifying at least one difference at the molecular level between at least two biological systems, the method comprising the steps of a) contacting a pool of oligonucleotides with target molecules of a first one of said biological systems, wherein some of oligonucleotides from said pool have an affinity for at least one of the target molecules of said first biological system;

b) separating the oligonucleotides having an affinity for said at least one target molecule from the remainder of the pool;

c) amplifying the oligonucleotides which have been separated in step b), to yield a pool enriched in oligonucleotides having a higher affinity for said at least one target molecule;

d) contacting the amplified oligonucleotides of step c) with target molecules of a second one of said biological systems;

e) removing the oligonucleotides having an affinity for any of the target molecules of said second biological system;

f) amplifying the remaining oligonucleotides to yield a pool of oligonucleotides having a higher affinity for said at least one target molecule of said first biological system and a lower affinity for any of the target molecules of said second biological system; and g) repeating the combination of steps a) to f) until at least one difference is identified.

2. A method for selecting oligonucleotides able of identifying at least one difference at the molecular level between at least two biological systems, the method comprising the steps of:

a) contacting a pool of oligonucleotides with target molecules of a first one of said biological systems, wherein some of oligonucleotides from said pool may have an affinity for one or more of the target molecules of said first biological system;

b) removing the oligonucleotides having an affinity for the one or more of the target molecules of said firs t biological system;

c) amplifying the remaining oligonucleotides to yield a pool enriched in oligonucleotides having a lower affinity for the target molecules of said first biological system;

d) contacting the amplified oligonucleotides of step c) with target molecules of a second one of said biological systems, wherein some of said oligonucleotides have an affinity for at least one of the target molecules of said second biological system;

e) separating the oligonucleotides having an affinity for said at least one target molecule from the remainder of the pool;

f) amplifying the oligonucleotides which have been separated in step e), to yield a pool of oligonucleotides having a lower affinity for the target molecules of said first biological system and a higher affinity for said at least one target molecule of said second biological system; and g) repeating the combination of steps a) to f) until at least one difference is identified.

3. The method of claim 1, wherein said method is carried out in parallel with a complementary method comprising the steps of:

a') contacting a pool of oligonucleotides with target molecules of a first one of said biological systems, wherein some of oligonucleotides from said pool may have an affinity for one or more of the target molecules of said first biological system;

b') removing the oligonucleotides having an affinity for the one or more of the target molecules of said first biological system;

c') amplifying the remaining oligonucleotides to yield a pool enriched in oligonucleotides having a lower affinity for the target molecules of said first biological system;

d') contacting the amplified oligonucleotides of step c') with target molecules of a second one of said biological systems, wherein some of said oligonucleotides have an affinity for at least one of the target molecules of said second biological system;

e') separating the oligonucleotides having an affinity for said at least one target molecule from the remainder of the pool;

f') amplifying the oligonucleotides which have been separated in step e'), to yield a pool of oligonucleotides having a lower affinity for the target molecules of said first biological system and a higher affinity for said at least one target molecule of said second biological system; and g') repeating the combination of steps a') to f') until at least one difference is identified.

4. A method for selecting oligonucleotides able of identifying at least one difference at the molecular level between at least two biological systems, the method comprising the steps of a) contacting a pool of oligonucleotides with target molecules of a first one of said biological systems, wherein some of oligonucleotides from said pool have an affinity for at least one of the target molecules of said first biological system;

b) separating the oligonucleotides having an affinity for said at least one target molecule from the remainder of the pool;

c) amplifying the oligonucleotides which have been separated in step b), to yield a pool enriched in oligonucleotides having a higher affinity for said at least one target molecule;

d) contacting the amplified oligonucleotides of step c) with target molecules of a second one of said biological systems;

e) removing the oligonucleotides having an affinity for any of the target molecules of said second biological system;

f) amplifying the remaining oligonucleotides to yield an amplified pool of oligonucleotides having a higher affinity for said at least one target molecule of said first biological system and a lower affinity for any of the target molecules of said second biological system;

g) fractionating the amplified pool of step f) in at least two portions;

h) contacting a first one of said portion with target molecules of said first biological system and separating the at least one target molecule to which oligonucleotides have an affinity from the remainder of the target molecules; and i) repeating the combination of steps a) to h) until at least one difference is identified, wherein in at least one of the subsequent steps a):

a second one of said portions is used as the pool of oligonucleotides;

only said at least one target molecule separated in step h) is used as target molecule of said first biological system.

5. The method of claim 4 wherein:

step h) further comprises the sub-steps h') of contacting a third one of said portions with target molecules of said second biological system, and separating any target molecule of said second biological system to which oligonucleotides have an affinity from the remainder of the target molecules of said second biological system;

in step i), for at least one of the subsequent steps d) during the repetition of the combination of steps a) to h), using only the target molecule(s) of said second biological system that have been separated in step h) as target molecule(s) of said second biological system.

6. The method of claim 5 wherein, during the contacting step h'), the target molecules of said second biological system have an increased concentration as compared to the previous contacting step d).

7. A method for selecting oligonucleotides able of identifying at least one difference at the molecular level between at least two biological systems, the method comprising the steps of:

a) contacting a pool of oligonucleotides with target molecules of a first one of said biological systems, wherein same of oligonucleotides from said pool may have an affinity for one or many of the target molecules of said first biological system;

b) removing the oligonucleotides having an affinity for one or many of the target molecules of said second biological system;

c) amplifying the remaining oligonucleotides, to yield a pool enriched in oligonucleotides having a lower affinity for the target molecules of said first biological system;

d) contacting the amplified oligonucleotides of step c) with target molecules of a second one of said biological systems, wherein some of said oligonucleotides have an affinity for at least one of the target molecules of said second biological system;

e) separating the oligonucleotides having an affinity for said at least one target molecule from the remainder of the pool;

f) amplifying the oligonucleotides which have been separated in step e) to yield an amplified pool of oligonucleotides having a lower affinity for the target molecules of said first biological system and a higher affinity for said at least one target molecule of said second biological;

g) fractionating the amplified pool of step f) in at least two portions;

h) contacting a first one of said portions with target molecules of said second biological system and separating the at least one target molecule to which oligonucleotides have an affinity from the remainder of the target molecules; and i) repeating the combination of steps a) to h) until at least one difference is identified, wherein in at least one of the subsequent steps d):
a second one of said portions is used as the pool of oligonucleotides;
only said at least one target molecule separated in step h) is used as target molecule of said second biological system.

8. The method of claim 7 wherein:
step h) further comprises the sub-steps h') of contacting a third one of said portions with target molecules of said first biological system, and separating any target molecule to which oligonucleotides have an affinity from the remainder of the target molecules of said first biological system;
in step i), for at least one of the subsequent steps a) during the repetition of the combination of steps a) to h), using only the target molecule(s) of said first biological system that have been separated in step h') as target molecule(s) of said first biological system.

9. The method of claim 8 wherein, during the contacting step h'), the target molecules of said first biological system have an increased concentration as compared to the previous contacting step a).

10. The method of claim 4, wherein said method is carded out in parallel with a complementary method comprising the steps of:

a') contacting a pool of oligonucleotides with target molecules of a first one of said biological systems, wherein some of oligonucleotides from said pool may have an affinity for one or many of the target molecules of said first biological system;

b') removing the oligonucleotides having an affinity for one or many of the target molecules of said second biological system;

c') amplifying the remaining oligonucleotides, to yield a pool enriched in oligonucleotides having a lower affinity for the target molecules of said first biological system;

d') contacting the amplified oligonucleotides of step c') with target molecules of a second one of said biological systems, wherein some of said oligonucleotides have an affinity for at least one of the target molecules of said second biological system;

e') separating the oligonucleotides having an affinity for said at least one target molecule from the remainder of the pool;

f') amplifying the oligonucleotides which have been separated in step e'), to yield an amplified pool of oligonucleotides having a lower affinity for the target molecules of said first biological system and a higher affinity for said at least one target molecule of said second biological;

g') fractionating the amplified pool of step f') in at least two portions;

h') contacting a first one of said portions with target molecules of said second biological system and separating the at least one target molecule to which oligonucleotides have an affinity from the remainder of the target molecules; and i') repeating the combination of steps a') to h') until at least one difference is identified, wherein in at least one of the subsequent steps d'):
a second one of said portions is used as the pool of oligonucleotides;
only said at least one target molecule separated in step h') is used as target molecule of said second biological system.

11. The method of claim 1, wherein said biological systems are selected from the group consisting of biological fluids, single cell, aggregate of cells, collection of cell types, aggregate of macromolecules, tissue, extracts and substructure isolation therefrom.

12. The method of claim 1, wherein said target molecules are selected from the group consisting of proteins, peptides, nucleic acids, carbohydrates, lipids, polysaccharides, glycoproteins, hormones, receptors, antigens, antibodies, virus, pathogens, chemical substances, substrates, metabolites, cofactors, inhibitors, drugs, dyes, nutrients, growth factors and cells.

13. The method of claim 1, wherein said oligonucleotides are single-stranded nucleic acids sequences and/or double-stranded nucleic acids sequences.

14. The method of claim 4, wherein said biological systems are selected from the group consisting of biological fluids, single cell, aggregate of cells, collection of cell types, aggregate of macromolecules, tissue, extracts and substructure isolation therefrom.

15. The method of claim 4, wherein said target molecules are selected from the group consisting of proteins, peptides, nucleic acids, carbohydrates, lipids, polysaccharides, glycoproteins, hormones, receptors, antigens, antibodies, virus, pathogens, chemical substances, substrates, metabolites, cofactors, inhibitors, drugs, dyes, nutrients, growth factors and cells.

16. The method of claim 4, wherein said oligonucleotides are single-stranded nucleic acids sequences and/or double-stranded nucleic acids sequences.

17. The method of claim 7, wherein said biological systems are selected from the group consisting of biological fluids, single cell, aggregate of cells, collection of cell types, aggregate of macromolecules, tissue, extracts and substructure isolation therefrom.

18. The method of claim 7, wherein said target molecules are selected from the group consisting of proteins, peptides, nucleic acids, carbohydrates, lipids, polysaccharides, glycoproteins, hormones, receptors, antigens, antibodies, virus, pathogens, chemical substances, substrates, metabolites, cofactors, inhibitors, drugs, dyes, nutrients, growth factors and cells.

19. The method of claim 7, wherein said oligonucleotides are single-stranded nucleic acids sequences and/or double-stranded nucleic acids sequences.

20. A method for identifying at least one difference at the molecular level between at least two biological systems, said method using oligonucleotides selected according to the method of claim 1, and comprising the steps of purifying and isolating from said first or second biological systems said at least one target molecule to which oligonucleotides have an affinity, said purifying and isolating steps being carried out using the affinity between said at least one target molecule and said oligonucleotides.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      CONSTRUCT

<400> SEQUENCE: 1
gtggactaag gcattgccag                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      CONSTRUCT

<400> SEQUENCE: 2
tggctagctt ccaggtctat                                                    20